(12) United States Patent
Vu et al.

(10) Patent No.: US 7,850,630 B1
(45) Date of Patent: Dec. 14, 2010

(54) FLEXIBLE HEAD SUPPORT WITH REPLACEABLE CHINREST

(75) Inventors: An Binh Vu, Carlsbad, CA (US); Gregory Philip Jordan, Carlsbad, CA (US)

(73) Assignee: Dupaco, Inc., Oceanside, CA (US)

( * ) Notice: Subject to any disclaimer, the term of this patent is extended or adjusted under 35 U.S.C. 154(b) by 390 days.

(21) Appl. No.: 12/026,237

(22) Filed: Feb. 5, 2008

(51) Int. Cl.
*A61F 5/00* (2006.01)

(52) U.S. Cl. .................. 602/17; 601/1; 601/5; 601/17; 601/18

(58) Field of Classification Search .................. 602/17, 602/18, 1, 5; 128/DIG. 23
See application file for complete search history.

(56) References Cited

U.S. PATENT DOCUMENTS 5,005,563 A * 4/1991 Veale ........................... 602/18
6,969,366 B1 11/2005 Reddick
2004/0204666 A1 * 10/2004 Marsh ......................... 602/18

\* cited by examiner

*Primary Examiner*—Patricia M Bianco
*Assistant Examiner*—Tarla R Patel
(74) *Attorney, Agent, or Firm*—Edward W. Callan

(57) ABSTRACT

Apparatus for supporting a person's head in a selected position includes a flexible shaft that will maintain its shape when reconfigured for enabling a person's head to be supported in a selected position and a first coupler attached to one end of the shaft for coupling a replaceable chinrest to the one end of the shaft in a releasable restraining engagement. The first coupler includes a protuberance that is shaped for fitting within a cavity of the replaceable chinrest. The first coupler is rotatable about the longitudinal axis of the shaft. A second coupler is attached to the other end of the shaft for coupling a replaceable support base to the other end of the shaft in a releasable restraining engagement. The second coupler includes a protuberance having a shape that is functionally equivalent to the shape of the protuberance of the first coupler.

17 Claims, 1 Drawing Sheet

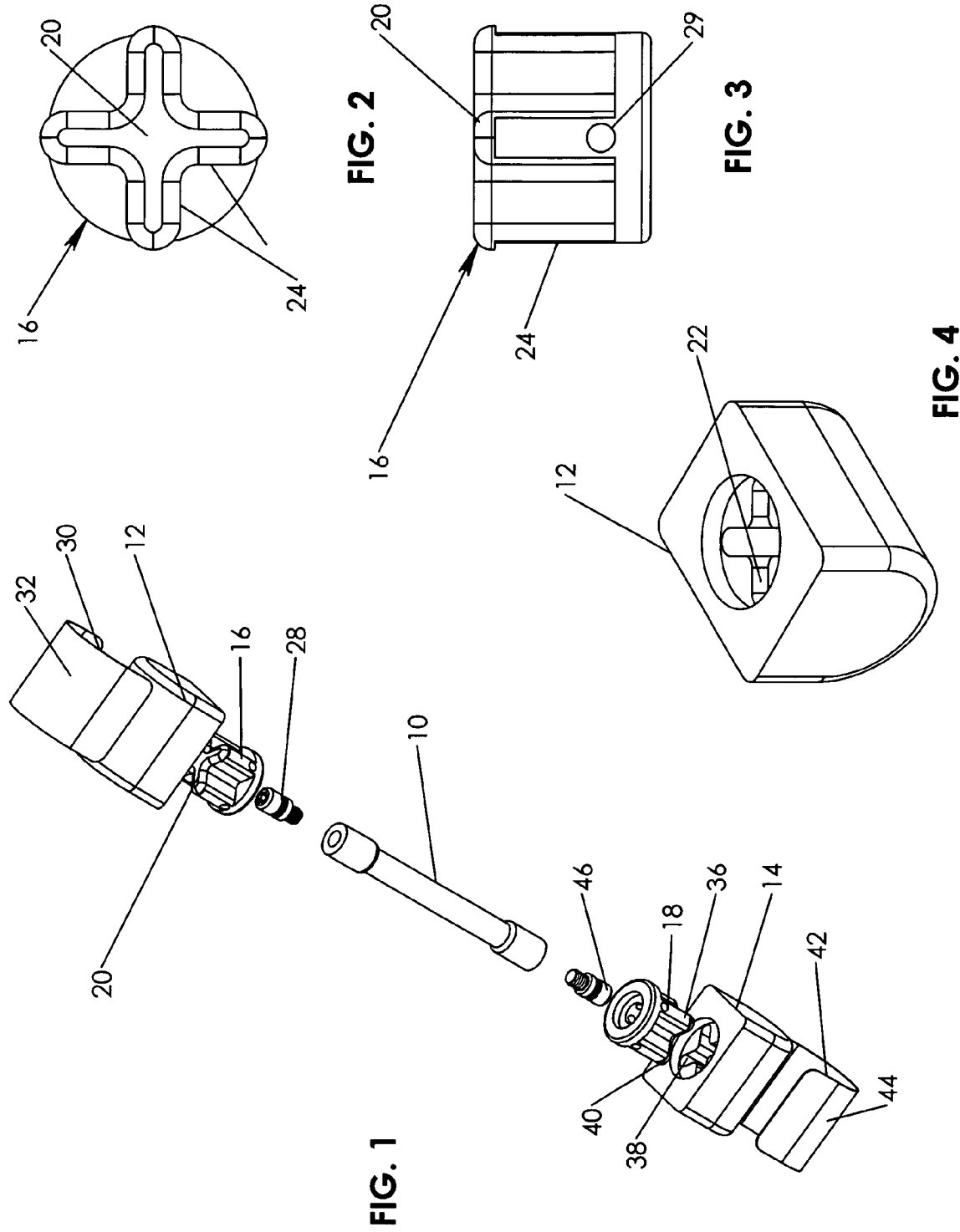

FLEXIBLE HEAD SUPPORT WITH REPLACEABLE CHINREST

BACKGROUND OF THE INVENTION

The present invention generally pertains to medical apparatus and is particularly directed to apparatus for supporting a person's head in a selected position.

Such an apparatus is described in U.S. Pat. No. 6,969,366 to Joan Reddick. The apparatus is a head support of unitary construction that includes a flexible shaft that will maintain its shape when reconfigured for enabling a person's head to be supported in a selected position; a chinrest attached to one end of the shaft; and a support base attached to the other end of the shaft. The shaft transfers the weight of a person's head to the support base when the support base has been placed upon the person's chest.

In the preferred embodiment, the flexible shaft, the chinrest and the support base are made of a flexible thermoplastic elastomer. The chinrest and the support base are attached to the shaft by virtue of the extrusion of liquid plastic. At the point of contiguity with the shaft the chin rest can be bent slightly up and down.

The head support described in U.S. Pat. No. 6,969,366 enables a patient's head to be supported in a selected position in which the patient's airway remains open while the patient is anesthetized, so that someone does not have to manually support the patient's lower jaw to assure that the airway remains open throughout a medical procedure that is being performed on the anesthetized patient.

SUMMARY OF THE INVENTION

The present invention provides improvements in the apparatus and assembly of a head support that includes a shaft and a chinrest for supporting a person's head.

The present invention provides apparatus for supporting a person's head in a selected position, comprising: a shaft; a coupler attached to one end of the shaft for coupling a replaceable chinrest to the one end of the shaft in a releasable restraining engagement; and a base attached to the other end of the shaft for enabling the shaft to be supported on the person's chest, wherein the shaft enables a person's head to be supported in a selected position in relation to the person's chest; and wherein the coupler includes either: at least one protuberance that is shaped for fitting within a cavity of a said replaceable chinrest so that the replaceable chinrest can be releaseably restrained by the coupler; or at least one cavity that is shaped for fitting about a protuberance of a said replaceable chinrest so that the replaceable chinrest can be releaseably restrained by the coupler; and wherein the base attached to the other end of the shaft comprises: a second coupler attached to the other end of the shaft for coupling a replaceable support base to the other end of the shaft in a releasable restraining engagement.

The present invention also provides a replaceable chinrest for use in an apparatus for supporting a person's head in a selected position, said apparatus including: a shaft; a coupler attached to one end of the shaft for coupling the replaceable chinrest to the one end of the shaft in a releasable restraining engagement; and a base attached to the other end of the shaft for enabling the shaft to be supported on the person's chest; wherein the shaft enables the person's head to be supported in a selected position in relation to the person's chest; and the coupler includes either at least one protuberance or at least one cavity, wherein either: the replaceable chinrest has a cavity that is shaped for fitting about a said at least one protuberance of the coupler so that the replaceable chinrest can be releaseably restrained by the coupler; or the replaceable chinrest has a protuberance that is shaped for fitting within a said at least one cavity of the coupler so that the replaceable chinrest can be releaseably restrained by the coupler; wherein the replaceable chinrest comprises: a foam cushion, with one side of the cushion being shaped for resting a person's chin, and another side of the cushion having either the cavity or the protuberance.

The inclusion of a replaceable chinrest in the head support enables one to dispose of the chinrest whenever necessary without having to dispose of the entire head support.

The present invention further provides a method of assembling a flexible head support, comprising the steps of:

(a) providing an apparatus for supporting a person's head in a selected position, said apparatus including: a shaft; a coupler attached to one end of the shaft for coupling the replaceable chinrest to the one end of the shaft in a releasable restraining engagement; and a base attached to the other end of the shaft for enabling the shaft to be supported on the person's chest; wherein the shaft enables the person's head to be supported in a selected position in relation to the person's chest; and wherein the coupler includes either at least one protuberance that is shaped for fitting within a cavity of a replaceable chinrest so that the replaceable chinrest can be releaseably restrained by the coupler or at least one cavity that is shaped for fitting about a protuberance of a replaceable chinrest so that the replaceable chinrest can be releaseably restrained by the coupler; wherein either: the replaceable chinrest has a cavity that is shaped for fitting about a said at least one protuberance of the coupler so that the replaceable chinrest can be releaseably restrained by the coupler; or the replaceable chinrest has a protuberance that is shaped for fitting within a said at least one cavity of the coupler so that the replaceable chinrest can be releaseably restrained by the coupler;

(b) providing a said replaceable chinrest that is shaped for being releaseably restrained by the coupler in a releasable restraining engagement; and (c) fitting the at least one protuberance into the cavity to thereby couple the replaceable chinrest to the one end of the shaft;

wherein the base attached to the other end of the shaft comprises a second coupler that is attached to the other end of the shaft, wherein the second coupler is for coupling a replaceable support base to the other end of the shaft in a releasable restraining engagement;

the method further comprising the steps of:

(d) providing a said replaceable support base; and (e) using the second coupler to couple the replaceable support base to the other end of the shaft.

Additional features of the present invention are described with reference to the detailed description of the preferred embodiments.

BRIEF DESCRIPTION OF THE DRAWING

FIG. 1 is an exploded perspective view of one embodiment of a head support apparatus according to the invention.

FIG. 2 is top view of the chinrest coupler included in the head support apparatus shown in FIG. 1.

FIG. 3 is side view of the chinrest coupler included in the head support apparatus shown in FIG. 1.

FIG. 4 is bottom view of the chinrest included in the head support apparatus shown in FIG. 1.

DETAILED DESCRIPTION

Referring to FIGS. 1-4, one embodiment of an apparatus according to the present invention includes a flexible shaft 10, a replaceable chinrest 12, a replaceable support base 14, a first coupler 16 and a second coupler 18.

The flexible shaft 10 is made of a material that will maintain its shape when reconfigured for enabling a person's head to be supported in a selected position. The shaft material is a malleable thermoplastic elastomer or one of the other shaft materials described in the aforementioned U.S. Pat. No. 6,969,366. The shaft 10 can be reconfigured by being bent.

The chinrest 12 is a foam cushion for resting a person's chin. In alternative embodiments (not shown), the chinrest is constructed of a material and/or has a configuration for resting the lower jaw as described in the aforementioned U.S. Pat. No. 6,969,366.

The first coupler 16 is attached to one end of the shaft 10 for coupling the replaceable chinrest 12 to the one end of the shaft 10 in a releasable restraining engagement. The first coupler includes at least one protuberance 20 that is shaped for fitting within the cavity 22 of the replaceable chinrest 12 so that the replaceable chinrest 12 can be releaseably restrained by the coupler 16. In the embodiment illustrated in FIGS. 1-4, the protuberance 20 includes a plurality of arms 24 and is cross-shaped. In alternative embodiments (not shown), the first coupler includes a plurality of protuberances for fitting within one or more cavities of a replaceable chinrest; the protuberance is other than cross-shaped; and/or does not have a plurality of arms.

The cavity 22 of the replaceable chinrest 12 is shaped for fitting about the cross-shaped protuberance 20 of the first coupler 16. In alternative embodiments (not shown), the chinrest includes one more cavities for fitting about whatever protuberance or protuberances are included in alternative embodiments of the first coupler.

The first coupler 16 is attached to the shaft 10 by a stud 28 so that the first coupler 16 is rotatable about the longitudinal axis of the shaft 10 at the one end of the shaft 10 to enable variation of the orientation of the chinrest 12 for supporting a person's head. Ball plungers (not shown) within openings 29 in the arms 24 of the first coupler 16 apply pressure against the studs 28 for controlling the ease with which the first coupler 16 can be rotated.

In alternative embodiments (not shown), the first coupler is attached to the shaft by some other device, such as a device that includes a bearing, that enables the orientation of the first coupler with respect to the longitudinal axis of the shaft at the one end of the shaft to be more variable than the variation in orientation that can be achieved by rotating the first coupler about the longitudinal axis of the shaft at the one end of the shaft.

An article 30 having an outer surface 32 that will retain the chin of a person in a stable position on the chinrest 12 is attached to the outer surface of the chinrest 12. In a preferred embodiment, the outer surface 32 of the article 30 includes an adhesive. In alternative embodiments, the outer surface 32 is one of the other materials for retaining the chin of a person on that chinrest that are described in the aforementioned U.S. Pat. No. 6,969,366.

The second coupler 18 is attached to the other end of the shaft 10 for coupling the replaceable support base 14 to the other end of the shaft 10 in a releasable restraining engagement. The second coupler 18 includes a protuberance 36 that is shaped for fitting within a cavity 38 of the replaceable support base 14 so that the support base 14 can be releaseably restrained by the second coupler 18. In the embodiment illustrated in FIG. 1, the protuberance 36 includes a plurality of arms 40 and is cross-shaped. In alternative embodiments (not shown), the second coupler includes a plurality of protuberances for fitting within one or more cavities of a replaceable support base; the protuberance is other than cross-shaped; and/or does not have a plurality of arms.

The replaceable support base 14 is a foam cushion having the same size and shape as the replaceable chinrest 12, whereby the replaceable support base 14 can be used either for holding the head support in place or for resting a person's chin. In alternative embodiments (not shown), the support base is constructed of a material and/or has a configuration as described in the aforementioned U.S. Pat. No. 6,969,366.

An article 42 having an outer surface 44 that will retain the support base 14 in a stable position on a person's chest is attached to the outer surface of the support base 14. In a preferred embodiment, the outer surface 44 of the article 42 includes an adhesive. In alternative embodiments, the outer surface 44 is one of the other materials for holding the head support in place that are described in the aforementioned U.S. Pat. No. 6,969,366.

In the embodiment shown in FIGS. 1-4, the shape of the second coupler 18 is functionally equivalent to the shape of the first coupler 16 so that a support base 14 having a cavity 38 that is functionally equivalent to the cavity 22 of the chinrest 12 can be fitted about the protuberance 36 and so that the chinrest 12 can be releaseably restrained by the second coupler 18. The replaceable chinrest 12 is shaped for being releaseably restrained by the first coupler 16 and for being releaseably restrained by the second coupler 18. Accordingly, the replaceable chinrest 12 and the replaceable support base 14 can be coupled interchangeably to either end of the shaft 10. In alternative embodiments (not shown), the shape of the protuberance of the second coupler is not functionally equivalent to the shape of the protuberance of the first coupler.

The second coupler 18 is attached to the shaft 10 by a stud 46 so that the second coupler 18 is rotatable about the longitudinal axis of the shaft 10 at the other end of the shaft 10 to enable variation of the orientation of the support base 14 on a person's chest. Ball plungers (not shown) within openings in the arms of the second coupler 18 apply pressure against the studs 46 for controlling the ease with which the second coupler 18 can be rotated.

In alternative embodiments (not shown), the second coupler is attached to the shaft by some other device, such as a device that includes a bearing, that enables the orientation of the second coupler with respect to the longitudinal axis of the shaft at the other end of the shaft to be more variable than the variation in orientation can be achieved by rotating the second coupler about the longitudinal axis of the shaft at the other end of the shaft.

The shaft 10 transfers the weight of a person's head to the support base 14 when the support base 14 has been placed upon the person's chest.

With the embodiment of the head support shown in FIGS. 1-4, the replaceable chinrest 12 and the replaceable support base 14 can be used interchangeably either for resting a person's chin or for holding the head support in place.

The flexible head support shown in FIGS. 1 and 2 is adjusted to select a position for supporting the person's head by (a) reconfiguring the shaft 10; (b) rotating the chinrest 12 about the longitudinal axis of the shaft 10 at the one end of the shaft 10; and (c) rotating the support base 14 about the longitudinal axis of the shaft 10 at the other end of the shaft 10.

In further alternative embodiments (not shown), (a) the replaceable chinrest includes at least one protuberance and the first coupler includes one or more cavities for fitting about the protuberance(s) of the chinrest so that the replaceable chinrest and the first coupler can be engaged in releasable restraining engagement; and/or (b) the replaceable support base includes at least one protuberance and the second coupler includes one or more cavities for fitting within the cavity or cavities of the support base so that the replaceable support base and the second coupler can be engaged in releasable restraining engagement; and/or (c) the first coupler and/or the second coupler is not attached to the shaft so that the orientation of the first coupler and/or the second coupler is adjustable with respect to the longitudinal axis of the shaft at the respective end of the shaft; and/or (d) a support base is attached to the shaft rather than being coupled thereto by a coupler in a releasable restraining engagement; and/or (e) the shaft is constructed so that it can be reconfigured by some technique other than, or in addition to, by being bent.

In still other embodiments the various aspects of the different embodiments described herein are combined with one another to the extent that they are not incompatible with each other.

The benefits specifically stated herein do not necessarily apply to every conceivable embodiment of the present invention. Further, such stated benefits of the present invention are only examples and should not be construed as the only benefits of the present invention.

While the above disclosure contains many specificities that may or may not be common to all of the embodiments described herein, these specificities are not to be construed as limitations on the scope of the present invention, but rather as examples of the preferred embodiments described herein. Other variations are possible and the scope of the present invention should be determined not by the embodiments described herein but rather by the claims and their legal equivalents. The claims require no implicit limitations. Each claim is to be construed explicitly as stated, or by its legal equivalent.

Regarding the method claims, except for those steps that can only occur in the sequence in which they are recited, and except for those steps for which the occurrence of a given sequence is specifically recited or must be inferred, the steps of the method claims do not have to occur in the sequence in which they are recited.

The invention claimed is:

1. Apparatus for supporting a person's head in a selected position, comprising:
    a shaft;
    a coupler attached to one end of the shaft for coupling a replaceable chinrest to the one end of the shaft in a releasable restraining engagement; and
    a base attached to the other end of the shaft for enabling the shaft to be supported on the person's chest,
    wherein the shaft enables a person's head to be supported in a selected position in relation to the person's chest; and
    wherein the coupler includes either:
    at least one protuberance that is shaped for fitting within a cavity of a said replaceable chinrest so that the replaceable chinrest can be releaseably restrained by the coupler; or
    at least one cavity that is shaped for fitting about a protuberance of a said replaceable chinrest so that the replaceable chinrest can be releaseably restrained by the coupler;
    wherein the at least one protuberance includes a plurality of arms.

2. Apparatus according to claim 1, wherein the at least one protuberance is cross-shaped.

3. Apparatus according to claim 1, further comprising a said replaceable chinrest that is shaped for being releaseably restrained by the coupler.

4. Apparatus according to claim 3, wherein the coupler includes said at least one protuberance; and
    wherein the replaceable chinrest includes a foam cushion, with one side of the cushion being shaped for resting a person's chin, and another side of the cushion having a cavity that is shaped for fitting about the at least one protuberance of the coupler.

5. Apparatus for supporting a person's head in a selected position, comprising:
    a shaft;
    a coupler attached to one end of the shaft for coupling a replaceable chinrest to the one end of the shaft in a releasable restraining engagement;
    a replaceable chinrest that is shaped for being releaseably restrained by the coupler;
    a base attached to the other end of the shaft for enabling the shaft to be supported on the person's chest,
    wherein the shaft enables a person's head to be supported in a selected position in relation to the person's chest; and
    wherein the coupler includes either:
    at least one protuberance that is shaped for fitting within a cavity of a said replaceable chinrest so that the replaceable chinrest can be releaseably restrained by the coupler; or
    at least one cavity that is shaped for fitting about a protuberance of a said replaceable chinrest so that the replaceable chinrest can be releaseably restrained by the coupler;
    wherein the coupler includes said at least one cavity; and
    wherein the replaceable chinrest includes a foam cushion, with one side of the cushion being shaped for resting a person's chin, and another side of the cushion having a protuberance that is shaped for fitting within the at least one cavity of the coupler.

6. Apparatus for supporting a person's head in a selected position, comprising:
    a shaft;
    a coupler attached to one end of the shaft for coupling a replaceable chinrest to the one end of the shaft in a releasable restraining engagement; and
    a base attached to the other end of the shaft for enabling the shaft to be supported on the person's chest,
    wherein the shaft enables a person's head to be supported in a selected position in relation to the person's chest; and
    wherein the coupler includes either:
    at least one protuberance that is shaped for fitting within a cavity of a said replaceable chinrest so that the replaceable chinrest can be releaseably restrained by the coupler; or
    at least one cavity that is shaped for fitting about a protuberance of a said replaceable chinrest so that the replaceable chinrest can be releaseably restrained by the coupler; and
    wherein the base attached to the other end of the shaft comprises:
    a second coupler attached to the other end of the shaft for coupling a replaceable support base to the other end of the shaft in a releasable restraining engagement.

7. Apparatus according to claim 6, wherein the second coupler includes either:

at least one protuberance that is shaped for fitting within a cavity of a said replaceable support base so that the support base can be releaseably restrained by the second coupler; or at least one cavity that is shaped for fitting about a protuberance of a said replaceable support base so that the replaceable support base can be releaseably restrained by the second coupler.

8. Apparatus according to claim 6, wherein the shape of the second coupler is functionally equivalent to the shape of the first-recited coupler so that the replaceable chinrest can be releaseably restrained by the second coupler.

9. Apparatus according to claim 8, further comprising a said replaceable chinrest that is shaped for being releaseably restrained by the first coupler and for being releaseably restrained by the second coupler.

10. A replaceable chinrest for use in an apparatus for supporting a person's bead in a selected position, said apparatus including: a shaft; a coupler attached to one end of the shaft for coupling the replaceable chinrest to the one end of the shaft in a releasable restraining engagement; and a base attached to the other end of the shaft for enabling the shaft to be supported on the person's chest; wherein the shaft enables the person's head to be supported in a selected position in relation to the person's chest; and the coupler includes either at least one protuberance or at least one cavity, wherein either:

the replaceable chinrest has a cavity that is shaped for fitting about a said at least one protuberance of the coupler so that the replaceable chinrest can be releaseably restrained by the coupler; or the replaceable chinrest has a protuberance that is shaped for fitting within a said at least one cavity of the coupler so that the replaceable chinrest can be releaseably restrained by the coupler;

wherein the replaceable chinrest comprises:

a foam cushion, with one side of the cushion being shaped for resting a person's chin, and another side of the cushion having either the cavity or the protuberance.

11. A method of assembling a flexible head support, comprising the steps of:

(a) providing an apparatus for supporting a person's head in a selected position, said apparatus including: a shaft; a coupler attached to one end of the shaft for coupling the replaceable chinrest to the one end of the shaft in a releasable restraining engagement; and a base attached to the other end of the shaft for enabling the shaft to be supported on the person's chest; wherein the shaft enables the person's head to be supported in a selected position in relation to the person's chest; and wherein the coupler includes either at least one protuberance that is shaped for fitting within a cavity of a replaceable chinrest so that the replaceable chinrest can be releaseably restrained by the coupler or at least one cavity that is shaped for fitting about a protuberance of a replaceable chinrest so that the replaceable chinrest can be releaseably restrained by the coupler; wherein the replaceable chinrest has a protuberance that is shaped for fitting within a said at least one cavity of the coupler so that the replaceable chinrest can be releaseably restrained by the coupler;

(b) providing a said replaceable chinrest that is shaped for being releaseably restrained by the coupler in a releasable restraining engagement; and (c) fitting the at least one protuberance into the cavity to thereby couple the replaceable chinrest to the one end of the shaft;

wherein the chinrest that is provided pursuant to step (a) includes a foam cushion, with one side of the cushion being shaped for resting a person's chin, and another side of the cushion having the protuberance.

12. A method according to claim 11, further comprising the step of:

(d) attaching to the chinrest an article having an outer surface that will retain the chin of a person in a stable position on the chinrest.

13. A method of assembling a flexible head support, comprising the steps of:

(a) providing an apparatus for supporting a person's head in a selected position, said apparatus including: a shaft; a coupler attached to one end of the shaft for coupling the replaceable chinrest to the one end of the shaft in a releasable restraining engagement; and a base attached to the other end of the shaft for enabling the shaft to be supported on the person's chest; wherein the shaft enables the person's head to be supported in a selected position in relation to the person's chest; and wherein the coupler includes either at least one protuberance that is shaped for fitting within a cavity of a replaceable chinrest so that the replaceable chinrest can be releaseably restrained by the coupler or at least one cavity that is shaped for fitting about a protuberance of a replaceable chinrest so that the replaceable chinrest can be releaseably restrained by coupler; wherein either: the replaceable chinrest has a cavity that is shaped for fitting about a said at least one protuberance of the coupler so that the replaceable chinrest can be releaseably restrained by the coupler; or the replaceable chinrest has a protuberance that is shaped for fitting within a said at least one cavity of the coupler so that the replaceable chinrest can be releaseably restrained by the coupler;

(b) providing a said replaceable chinrest that is shaped for being releaseably restrained by the coupler in a releasable restraining engagement; and (c) fitting the at least one protuberance into the cavity to thereby couple the replaceable chinrest to the one end of the shaft;

wherein the base attached to the other end of the shaft comprises a second coupler that is attached to the other end of the shaft, wherein the second coupler is for coupling a replaceable support base to the other end of the shaft in a releasable restraining engagement;

the method further comprising the steps of:

(d) providing a said replaceable support base; and (e) using the second coupler to couple the replaceable support base to the other end of the shaft.

14. A method according to claim 13, wherein steps (b) and (d) comprise providing a said chinrest and a said support base that are interchangeable with one another in that each is shaped for being releaseably restrained by the first coupler and for being releaseably restrained by the second coupler.

15. A method according to claim 13, further comprising the step of:

(f) attaching to the replaceable support base an article having an outer surface that will retain the support base in a stable position on a surface on which the support base is subsequently disposed.

16. A method of assembling a flexible head support, comprising the steps of:

(a) providing an apparatus for supporting a person's head in a selected position, said apparatus including: a shaft; a coupler attached to one end of the shaft for coupling the replaceable chinrest to the one end of the shaft in a releasable restraining engagement; and a base attached to the other end of the shaft for enabling the shaft to be supported on the person's chest; wherein the shaft enables the person's head to be supported in a selected position in relation to the person's chest; and wherein the coupler includes either at least one protuberance that shaped for within a cavity of a replaceable chinrest so that the replaceable chinrest can be releaseably restrained by the coupler or at least one cavity that is shaped for fitting about a protuberance of a replaceable chinrest so that the replaceable chinrest cap be releaseably restrained by the coupler; wherein either: the replaceable chinrest has a cavity that is shaped for fitting about a said at least one protuberance of the coupler so that the replaceable chinrest can be releaseably restrained by the coupler; or the replaceable chinrest has a protuberance that is shaped for fitting within a said, at least one cavity of the coupler so that the replaceable chinrest can be releaseably restrained by the coupler;

(b) providing a said replaceable chinrest that is shaped for being releaseably restrained by the coupler in a releasable restraining engagement; and (c) fitting the at least one protuberance into the cavity to thereby couple the replaceable chinrest to the one end of the shaft;

wherein the second coupler includes either at least one protuberance that is shaped for fitting within a cavity of the replaceable support base so that the replaceable support base can be releaseably restrained by the second coupler or at least one cavity that is shaped for fitting about a protuberance of a said replaceable support base so that the replaceable support base can be releaseably restrained by the second coupler;

wherein step (d) includes providing a said replaceable support base that is shaped for being releaseably restrained by the second coupler in a releasable restraining engagement; and wherein step (e) includes the step of either:

(f) fitting the at least one protuberance of the second coupler into the cavity of the support base; or (g) fitting the at least one protuberance of the support base into the cavity of the second coupler.

17. A method according to claim 16, wherein the support base that is provided pursuant to step (d) includes a foam cushion, with one side of the cushion being shaped for disposition upon a person's chest, and another side of the cushion having either a cavity that is shaped for fitting about the protuberance of the second coupler or a protuberance that is shaped for fitting within said at least one cavity of the second coupler.

* * * * *

UNITED STATES PATENT AND TRADEMARK OFFICE
CERTIFICATE OF CORRECTION

| | | |
|---|---|---|
| PATENT NO. | : 7,850,630 B1 | |
| APPLICATION NO. | : 12/026237 | |
| DATED | : December 14, 2010 | |
| INVENTOR(S) | : Vu et al. | |

It is certified that error appears in the above-identified patent and that said Letters Patent is hereby corrected as shown below:

at column 9, line 6, --is-- should be inserted before --shaped--
  at column 9, line 6, --fitting-- should be inserted before --within--
  at column 9, line 10, "cap" should be --can--
  at column 9, line 16, the "," after --said-- should be omitted Signed and Sealed this
Seventh Day of June, 2011

David J. Kappos
*Director of the United States Patent and Trademark Office*